US012685717B2

(12) United States Patent
Sah et al.

(10) Patent No.: US 12,685,717 B2
(45) Date of Patent: Jul. 21, 2026

(54) SUPPRESSION OF INFLAMMASOME ACTIVATION

(71) Applicants: Washington University, St. Louis, MO (US); Senseion Therapeutics, Inc., St. Louis, MO (US)

(72) Inventors: Rajan Sah, St. Louis, MO (US); Hongzhen Hu, St. Louis, MO (US); Ashutosh Kumar, St. Louis, MO (US); Daniel Lerner, St. Louis, MO (US)

(73) Assignees: Washington University, St. Louis, MO (US); Senseion Therapeutics, Inc., St. Louis, MO (US)

( * ) Notice: Subject to any disclaimer, the term of this patent is extended or adjusted under 35 U.S.C. 154(b) by 873 days.

(21) Appl. No.: 17/791,712

(22) PCT Filed: Jan. 11, 2021

(86) PCT No.: PCT/US2021/012983

§ 371 (c)(1),
(2) Date: Jul. 8, 2022

(87) PCT Pub. No.: WO2021/142450

PCT Pub. Date: Jul. 15, 2021

(65) Prior Publication Data

US 2023/0338311 A1 Oct. 26, 2023

Related U.S. Application Data

(60) Provisional application No. 62/959,775, filed on Jan. 10, 2020, provisional application No. 62/959,053, filed on Jan. 9, 2020.

(51) Int. Cl.

| | |
|---|---|
| ***A61K 31/192*** | (2006.01) |
| ***A61K 31/138*** | (2006.01) |
| ***A61K 31/41*** | (2006.01) |
| ***A61P 29/00*** | (2006.01) |

(52) U.S. Cl.

CPC .......... *A61K 31/192* (2013.01); *A61K 31/138* (2013.01); *A61K 31/41* (2013.01); *A61P 29/00* (2018.01)

(58) Field of Classification Search

CPC .... A61K 31/192; A61K 31/138; A61K 31/41; A61P 29/00; A61P 19/02

See application file for complete search history.

(56) References Cited

U.S. PATENT DOCUMENTS

| | | | |
|---|---|---|---|
| 3,984,465 | A | 10/1976 | Cragoe, Jr. et al. |
| 4,081,554 | A | 3/1978 | Cragoe, Jr. et al. |
| 10,039,772 | B2 | 8/2018 | Sanna |

FOREIGN PATENT DOCUMENTS

| | | | |
|---|---|---|---|
| WO | 2004/063148 | A1 | 7/2004 |
| WO | 2017/142855 | A1 | 8/2017 |
| WO | 2018/027175 | A1 | 2/2018 |
| WO | 2019/109188 | A1 | 6/2019 |
| WO | 2020/252018 | A1 | 12/2020 |
| WO | 2020/252041 | A1 | 12/2020 |

OTHER PUBLICATIONS

Courtney et al. (Pediatric Critical Care Medicine 18(4):p. 304-309, Apr. 2017). (Year: 2017).*

Choi, Hyehun et al., LRRC8A channels support TNFa-induced superoxide production by Nox1 which is required for receptor endocytosis, Free Radical Biology and Medicine 101 (2016) pp. 413-423.

Extended European Search Report dated Dec. 15, 2023 related to European Patent Application No. 21738815.6, 10 pages.

Compan et al., "Cell Volume Regulation Modulates NLRP3 Inflammasome Activation," Immunity, 37(3):487-500, Sep. 2012.

Daniels et al., "Fenamate NSAIDs Inhibit the NLRP3 Inflammasome and Protect Against Alzheimer's Disease in Rodent Models," Nat. Commun., 7:12504, Aug. 2016.

Feske et al., "Ion Channels in Innate and Adaptive Immunity," Annu Rev Immunol., 33:291-353, Mar. 2015.

Friedman et al., "Mechanisms of NAFLD Development and Therapeutic Strategies," Nat Med., 24(7):908-922, Jul. 2018.

Green et al., "Chloride Regulates Dynamic NLRP3-Dependent ASC Oligomerization and Inflammasome Priming," Proc Natl Acad Sci USA, 115(40):E9371-E9380, Oct. 2018.

Guo et al., "Inflammasomes: Mechanism of Action, Role in Disease, and Therapeutics," Nat Med., 21(7):677-687, Jul. 2015.

Hong et al., "Alteration of Volume-Regulated Chloride Channel During Macrophage-Derived Foam Cell Formation in Atherosclerosis," Atherosclerosis, 216(1):59-66, May 2011.

Ioannou et al., "Cholesterol Crystals in Hepatocyte Lipid Droplets Are Strongly Associated With Human Nonalcoholic Steatohepatitis," Hepatol Commun., 3(6):776-791, Jun. 2019.

Ioannou et al., "Cholesterol Crystallization Within Hepatocyte Lipid Droplets and Its Role in Murine NASH," J Lipid Res., 58(6):1067-1079, Jun. 2017.

Ioannou et al., "Hepatic Cholesterol Crystals and Crown-Like Structures Distinguish NASH From Simple Steatosis," J Lipid Res., 54(5):1326-1334, May 2013.

International Search Report and Written Opinion of the ISA/US in PCT/US2021/012983, dated May 13, 2021; 11pgs.

International Preliminary Report on Patentability of the International Bureau of WIPO in PCT/US2021/012983, dated Jul. 21, 2022; 8pgs.

Prasad et al., "Cyclic Nucleotides, Gut Physiology and Inflammation," FEBS J, 287(10):1970-1981, May 2020.

Pubmed Compound Record for CID 90195570, "1-[(2-Cyclopentyl-6,7-dimethyl-1-oxo-2,3-dihydroinden-5-yl)oxymethyl]-4-phenylcyclohexa-2,5-diene-1-carboxylic acid," U.S. National Library of Medicine, Feb. 13, 2015, pp. 1-8; (https://pubchem.ncbi.nlm.nih.gov/compound/90195570); p. 2.

(Continued)

*Primary Examiner* — Umamaheswari Ramachandran
(74) *Attorney, Agent, or Firm* — Stinson LLP

(57) ABSTRACT

The present invention is directed to various methods of suppressing inflammasome activation. For example, the present invention relates to various methods of treating a disease or condition in which inflammation contributes to the disease or condition state.

11 Claims, 8 Drawing Sheets

(56) References Cited

OTHER PUBLICATIONS

Wu et al., "Reduction of Intracellular Chloride Concentration Promotes Foam Cell Formation," Circ J., Vascular Biology and Vascular Medicine, 80(4):1024-1033, Mar. 2016.

* cited by examiner

Racemic analogs

SN-401/DCPIB

SN-403

SN-406

SN-407

SN-071

SN-072

SUPPRESSION OF INFLAMMASOME ACTIVATION

FIELD OF THE INVENTION

The present invention is directed to various methods of suppressing inflammasome activation. For example, the present invention relates to various methods of treating a disease or condition in which inflammation contributes to the disease or condition state.

BACKGROUND OF THE INVENTION

Inflammosome activation, especially dysregulation of inflammasome activation, is implicated in a wide range of inflammatory diseases such as rheumatologic and connective tissue diseases including rheumatic arthritis, systemic sclerosis and systemic lupus erythematosus. Other major inflammatory diseases include those of the gastrointestinal system such inflammatory bowel disease including ulcerative colitis and Crohn's disease, nonalcoholic inflammatory bowel steatohepatitis and fibrosis, alcoholic hepatitis, and autoimmune hepatitis. Still other inflammatory conditions include immunologic rejection of organ and tissue transplants. There remains an urgent need for therapeutics that are effective in suppressing inflammasome activation and treating these diseases.

BRIEF SUMMARY

Various aspects of the present invention are directed to methods of suppressing inflammasome activation. In various embodiments, methods for suppressing inflammasome activation in a subject in need thereof comprises administering to a subject a therapeutically effective amount of DCPIB (4-[2[butyl-6,7-dichloro-2-cyclopentyl-2,3-dihydro-1-oxo-1H-inden-5-yl)oxy]butanoic acid) or a congener thereof. In some embodiments, the method comprises administering to a subject a therapeutically effective amount of a compound selected from the group consisting of:

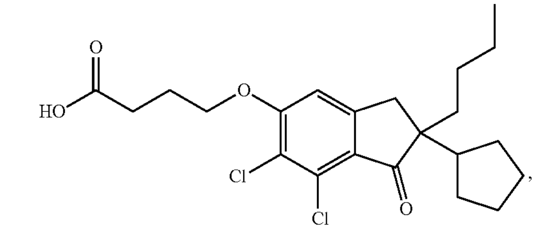

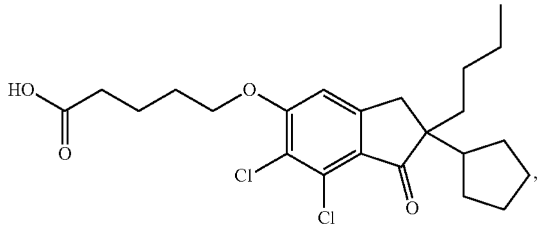

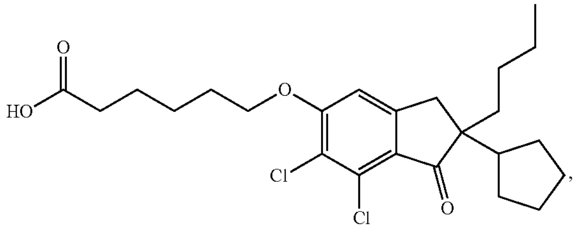

-continued

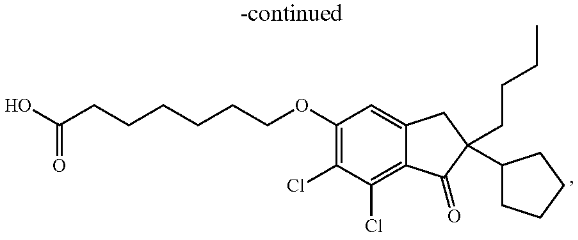

and salts thereof.

In various embodiments, the methods comprise administering to a subject a therapeutically effective amount of a compound of Formula (I), or a salt thereof:

(I)

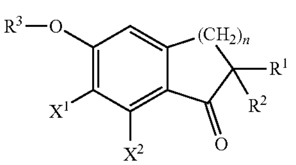

wherein $R^1$ and $R^2$ are each independently hydrogen, substituted or unsubstituted alkyl, substituted or unsubstituted alkenyl, substituted or unsubstituted alkoxy, substituted or unsubstituted aryl, substituted or unsubstituted heteroaryl; $R^3$ is —Y—C(O)$R^4$, —Z—N($R^5$)($R^6$), or -Z-A; $R^4$ is hydrogen, substituted or unsubstituted alkyl, —$ON^7$, or —N($R^8$)($R^9$); $X^1$ and $X^2$ are each independently substituted or unsubstituted alkyl, halo, —$OR^{10}$, or —N($R^{11}$)($R^{12}$); $R^5$, $R^6$, $R^7$, $R^8$, $R^9$, $R^{10}$, $R^{11}$, and $R^{12}$ are each independently hydrogen or substituted or unsubstituted alkyl; Y and Z are each independently a substituted or unsubstituted carbon-containing moiety having at least 2 carbon atoms; A is a substituted or unsubstituted 5- or 6-membered heterocyclic ring having at least one nitrogen heteroatom, boronic acid or

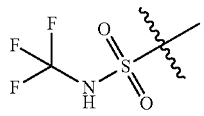 ;

and n is 1 or 2.

In various embodiments, the methods of suppressing inflammasome activation include treating a disease or condition in which inflammation contributes to the disease or condition state.

Other objects and features will be in part apparent and in part pointed out hereinafter.

DETAILED DESCRIPTION

Various aspects of the present invention are directed to methods of suppressing inflammasome activation (inflammation), which is implicated and central to a wide range of diseases and conditions. It has been discovered that targeting SWELL1 channels via SWELL1 inhibitors can effectively modulate the inflammatory response.

Figure 1:
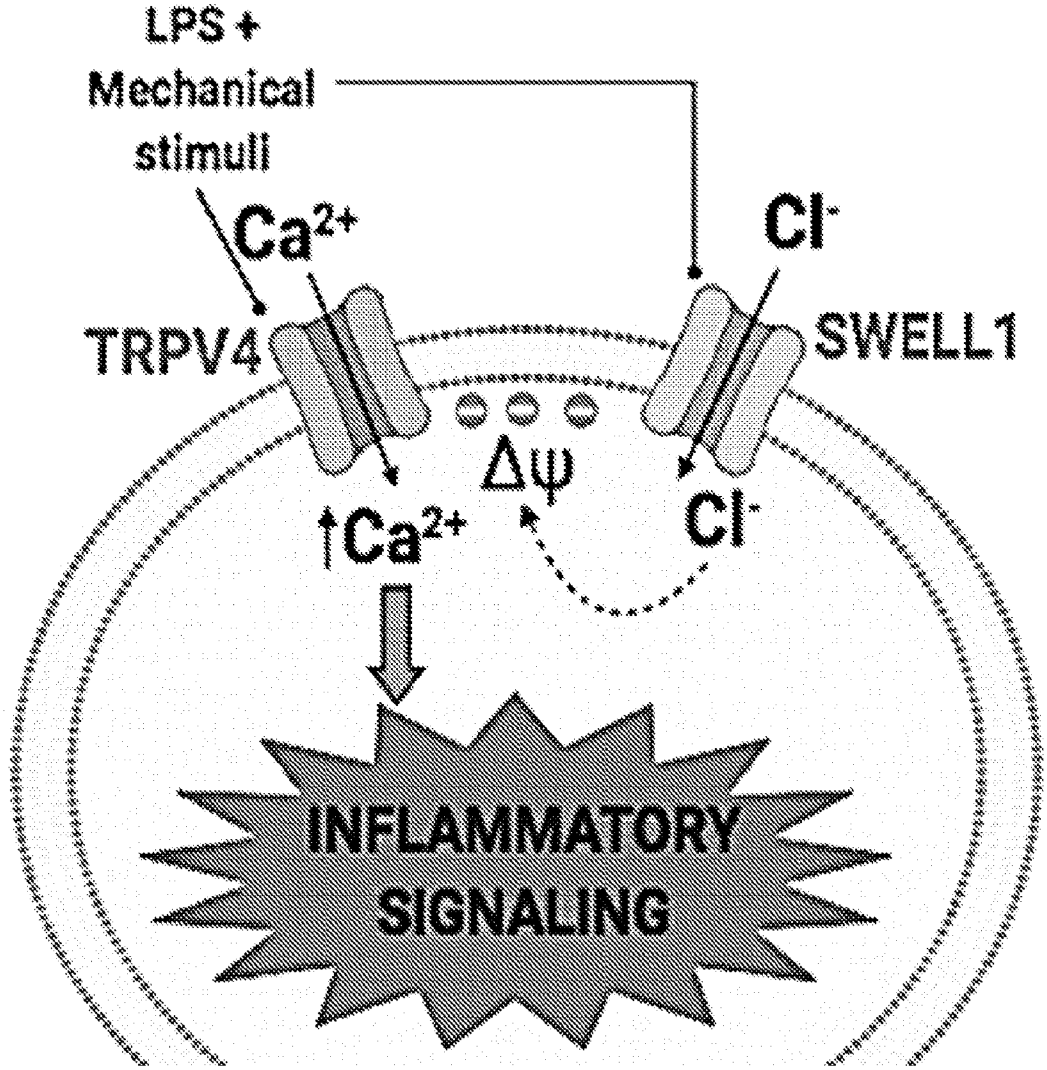
FIG. 1: SWELL1 regulation of TRPV4 dependent mechanism.

Mechanical stimuli and cell swelling can activate inflammation and inflammasome activity in various physiological and pathophysiological contexts. In the mechano-activation of inflammatory signaling, TRPV4 ion channels, which are believed to be mechanoresponsive, are thought to implicated in mediating the $Ca^{2+}$ influx required to activate the inflammasome and cellular inflammation. One model is depicted in FIG. 1. In this model, SWELL1-LRRC8 anion ($Cl^-$) channels are broadly expressed, and also expressed in macrophages that mediate this inflammatory response. In response to an inflammatory stimulus (LPS)+/− mechanical stimulation, both TRPV4 and SWELL1 channels open. TRPV4 channels provide the stimulatory $Ca^{2+}$ signal, while SWELL1 provides hyperpolarizing $Cl^-$ influx that serves to hyperpolarize the cell (drive the membrane potential down), and this further potentiates $Ca^{2+}$ via TRPV4, by increasing the driving force for $Ca^{2+}$ influx. In this way, SWELL1 channels function as amplifiers to regulate TRPV4 activation of the inflammasome, and inflammation. Therefore, SWELL1 inhibitors can dampen the inflammatory response, by down-regulating TRPV4—where TRPV4 is a known and validated target for inflammation and inflammasome activation.

Figure 2:
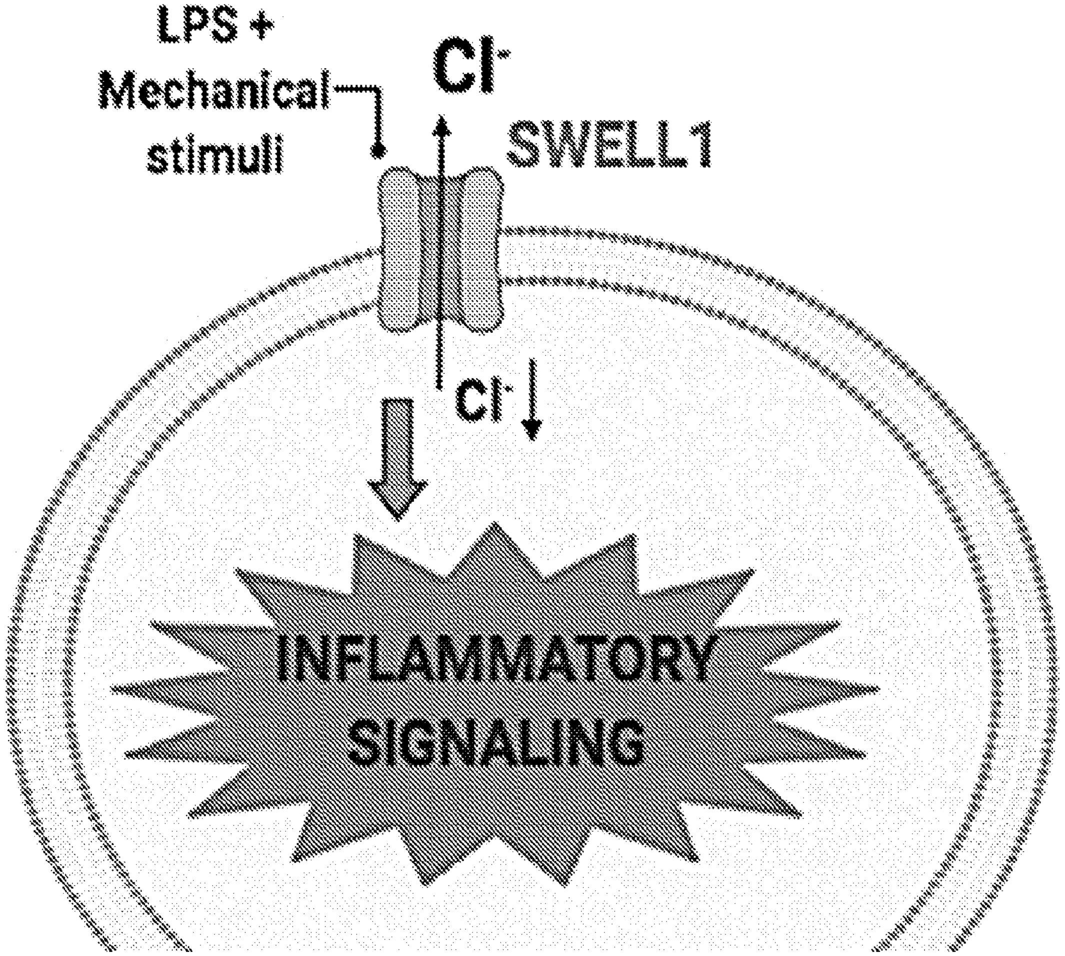
FIG. 2: SWELL1 dependent, TRPV4 independent mechanism.

A second model is depicted in FIG. 2. Intracellular chloride alone can regulate inflammatory signaling in macrophages. It has been shown that VRAC and VRAC inhibitors specifically have anti-inflammatory activity, via chloride-dependent and TRPV4 independent mechanisms. For example, VRAC activation promotes oxidized LPL-induced lipid accumulation in macrophage. It has been shown that opening of VRAC caused Cl efflux and reduction in intracellular [Cl]. See Hong et al., "Alteration of volume-regulated chloride channel during macrophage-derived foam cell formation in atherosclerosis," Atherosclerosis, Volume 216, Issue 1, May 2011, Pages 59-66. Also, reduction in intracellular [Cl] promotes a significant amount of signaling (JNK-p38) that leads to lipid accumulation in macrophage. See Wu et al., "Reduction of Intracellular Chloride Concentration Promotes Foam Cell Formation," Vascular Biology and Vascular Medicine, 2016 Volume 80 Issue 4 Pages 1024-1033. Thus, in this model, SWELL1 mediated chloride current promotes chloride efflux and this reduces the intracellular chloride concentration. Reductions in intracellular chloride are understood to inhibit NFkB mediated inflammatory pathway activation in a TRPV4 independent fashion.

Accordingly, in various embodiments, methods for suppressing inflammasome activation in a subject in need thereof comprises administering to a subject a therapeutically effective amount of a SWELL 1 inhibitor such as DCPIB (4-[(2-butyl-6,7-dichloro-2-cyclopentyl-1-oxo-2,3-dihydro-1H-inden-5-yl)oxy]butanoic acid) or a congener thereof. In some embodiments, the method comprises administering to a subject a therapeutically effective amount of a compound (SWELL1 inhibitor) selected from the group consisting of:

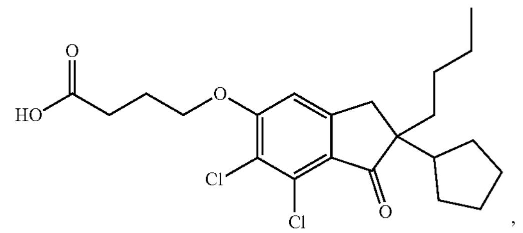
,

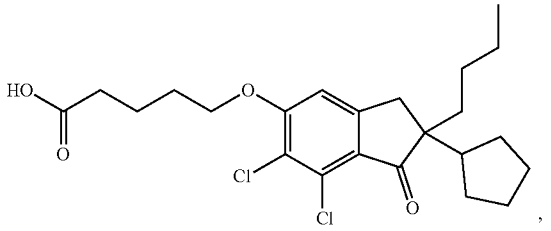
,

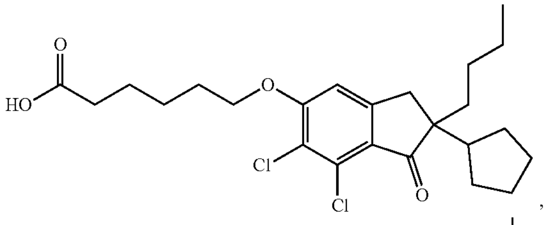
,

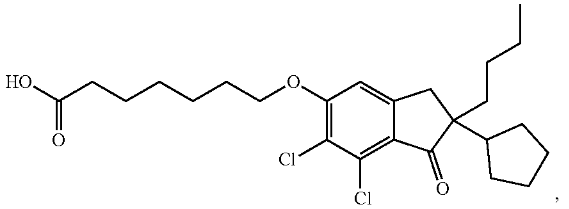
, and salts thereof.

In various embodiments, the methods comprise administering to a subject a therapeutically effective amount of a compound of Formula (I), and salts thereof:

(I)

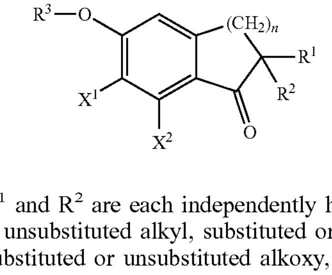

wherein $R^1$ and $R^2$ are each independently hydrogen, substituted or unsubstituted alkyl, substituted or unsubstituted alkenyl, substituted or unsubstituted alkoxy, substituted or unsubstituted aryl, substituted or unsubstituted heteroaryl; $R^3$ is —Y—C(O)$R^4$, —Z—N($R^5$)($R^6$), or -Z-A; $R^4$ is hydrogen, substituted or unsubstituted alkyl, —O$N^7$, or —N($R^8$)

($R^9$); $X^1$ and $X^2$ are each independently substituted or unsubstituted alkyl, halo, —$OR^{10}$, or —$N(R^{11})(R^{12})$; $R^5$, $R^6$, $R^7$, $R^8$, $R^9$, $R^{10}$, $R^{11}$, and $R^{12}$ are each independently hydrogen or substituted or unsubstituted alkyl;

Y and Z are each independently a substituted or unsubstituted carbon-containing moiety having at least 2 carbon atoms; A is a substituted or unsubstituted 5- or 6-membered heterocyclic ring

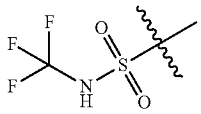;

having at least one nitrogen heteroatom, boronic acid or and n is 1 or 2.

In various embodiments, at least one of $R^1$ or $R^2$ is a substituted or unsubstituted linear or branched alkyl having at least 2 carbon atoms. In further embodiments, $R^1$ is hydrogen or a C1 to C6 alkyl. For example, in some embodiments, $R^1$ is butyl. In various embodiments, $R^2$ is cycloalkyl (e.g., cyclopentyl).

In various embodiments, $R^1$ and $R^2$ are selected from the group consisting of:

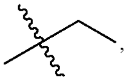, 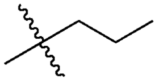, 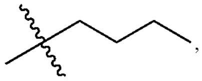,

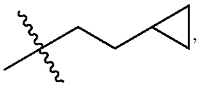, 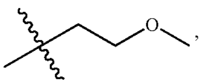,

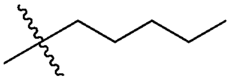, 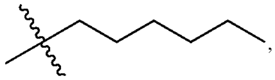,

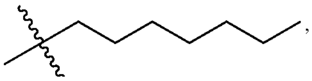, 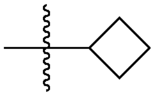,

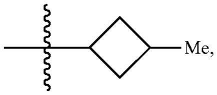 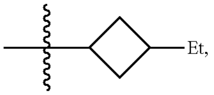

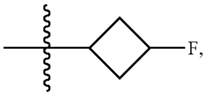 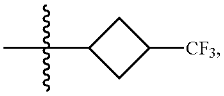

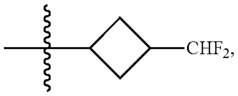 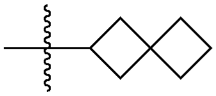,

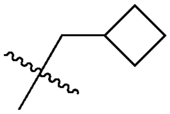, 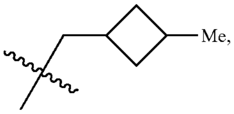

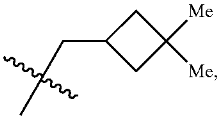 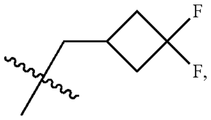

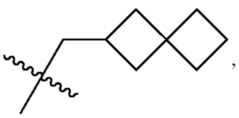, 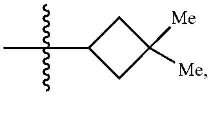

-continued

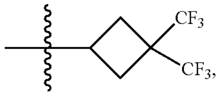 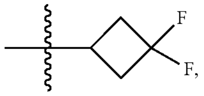

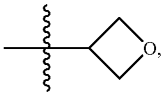 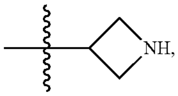 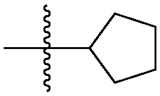

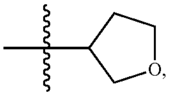 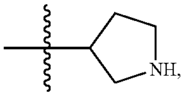 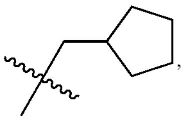

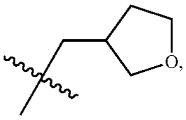 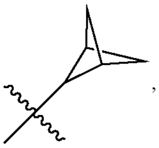, and

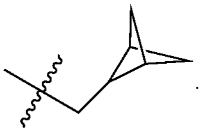.

In various embodiments, $R^3$ is —Y—C(O)$R^4$. In some embodiments, $R^3$ is —Z—$N(R^5)(R^6)$. In further embodiments, $R^3$ is -Z-A.

As noted above, A can be a substituted or unsubstituted 5- or 6-membered heterocyclic ring having at least one nitrogen heteroatom. In some embodiments, A is a substituted or unsubstituted 5- or 6-membered heterocyclic ring having at least two, three, or four nitrogen heteroatoms. In some embodiments, A is a substituted or unsubstituted 5- or 6-membered heterocyclic ring having at least one nitrogen heteroatom and at least one other heteroatom selected from oxygen or sulfur. In various embodiments, A can be boronic acid or

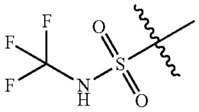.

In various embodiments, A is:

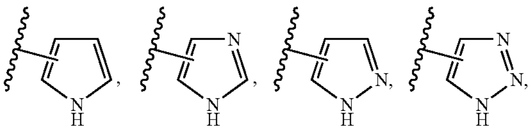

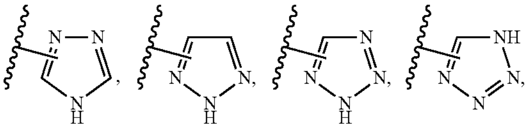

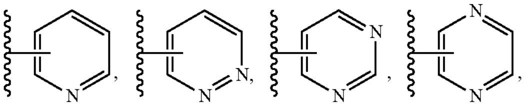

-continued

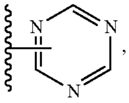, 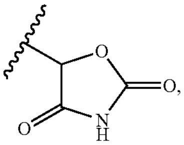, 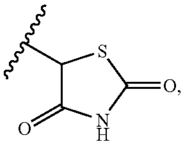,

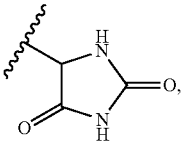, 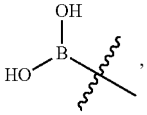, or

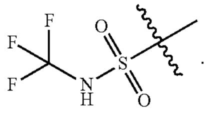.

In certain embodiments, A is

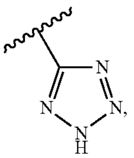, 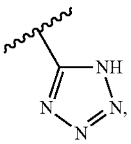, 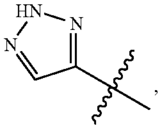,

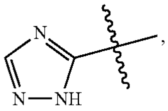, 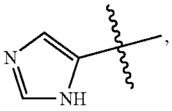, 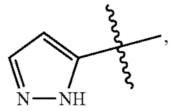,

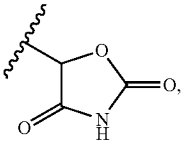, 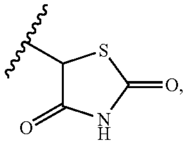, 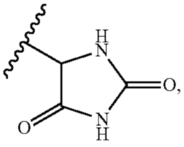,

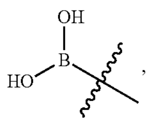, or 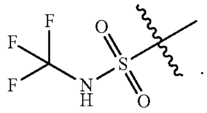.

In certain embodiments, $R^3$ is selected from the group consisting of:

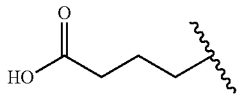, 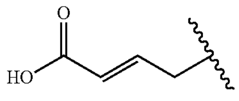,

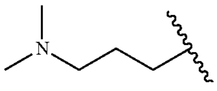, 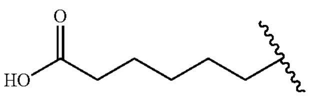,

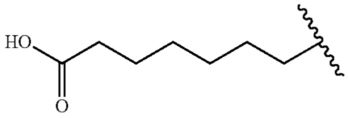,

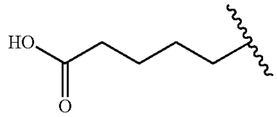,

-continued

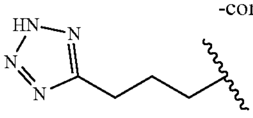, and 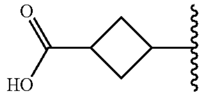.

In various embodiments, $R^4$ is —$ON^7$ or —$N(R^8)(R^9)$.

In various embodiments, $X^1$ and $X^2$ are each independently substituted or unsubstituted C 1 to C6 alkyl or halo. In some embodiments, $X^1$ and $X^2$ are each independently C1 to C6 alkyl, fluoro, chloro, bromo, or iodo. In certain embodiments, $X^1$ and $X^2$ are each independently methyl, fluoro, or chloro.

In various embodiments, $R^5$, $R^6$, $R^7$, $R^8$, $R^9$, $R^{10}$, $R^{11}$, and $R^{12}$ are each independently hydrogen or alkyl. For example, in some embodiments, $R^5$, $R^6$, $R^7$, $R^8$, $R^9$, $R^{10}$, $R^{11}$, and $R^{12}$ are each independently hydrogen or a C1 to C3 alkyl.

In various embodiments, Y and Z are each independently substituted or unsubstituted alkylene having 2 to 10 carbons, substituted or unsubstituted alkenylene having from 2 to 10 carbons, or substituted or unsubstituted arylene. In some embodiments, Y and Z are each independently alkylene having 2 to 10 carbons, alkenylene having from 2 to 10 carbons, or phenylene. Y and Z can also each independently be cycloalkylene having 4 to 10 carbons. In certain embodiments, Y is an alkylene or an alkenylene having 3 to 8 carbons or 3 to 7 carbons. For example, Y can be an alkylene or any alkenylene having 4 carbons. In further embodiments, Z is an alkylene having 2 to 4 carbons. For example, Z can be an alkylene having 3 or 4 carbons.

In various embodiments, Y or Z can be selected from the group consisting of

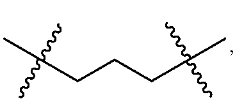, 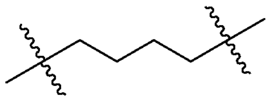,

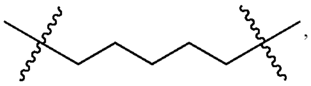,

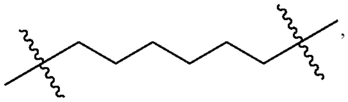,

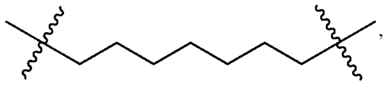,

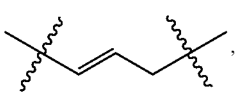, 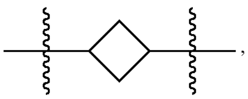,

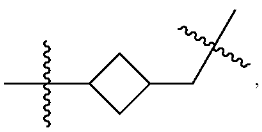, 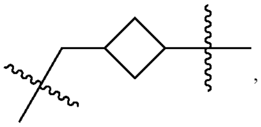,

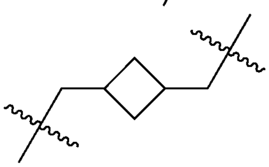,

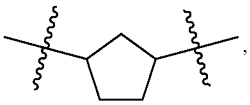, and 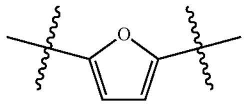.

In various embodiments, when Y is an alkylene having 2 to 3 carbons then both $X^1$ and $X^2$ are each fluoro or each substituted or unsubstituted alkyl (e.g., methyl or ethyl). In some embodiments, Y is not an alkylene having 3 carbons. In certain embodiments, $R^7$ is not hydrogen or a C1 to C6 alkyl. In some embodiments, $X^1$ and/or $X^2$ are not halo. In certain embodiments, $X^1$ and/or $X^2$ are not chloro. In some embodiments, $R^1$ and/or $R^2$ are not alkyl.

In accordance with the embodiments, the compound of Formula (I) may be selected from the group consisting of:

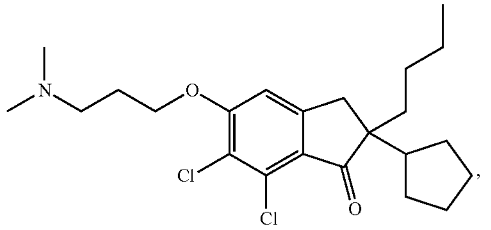
,
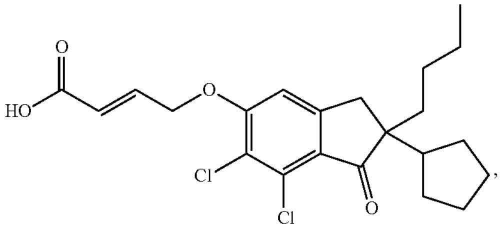
,
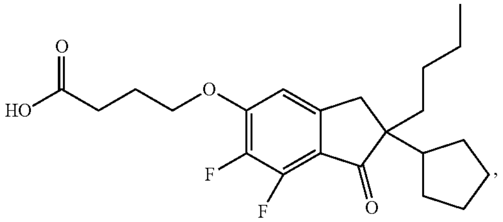
,
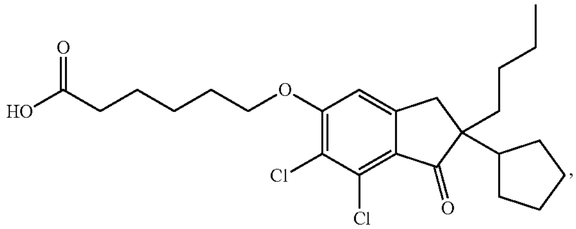
,
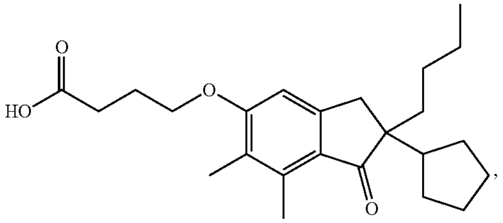
,
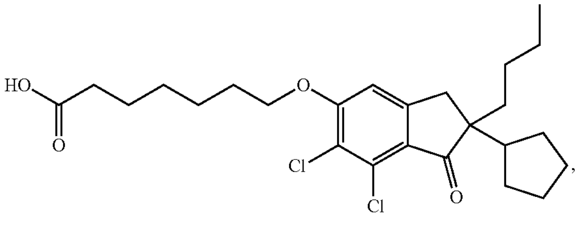
, -continued

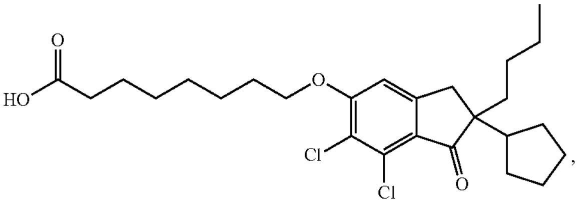
,
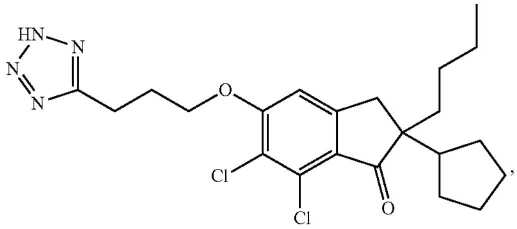
,
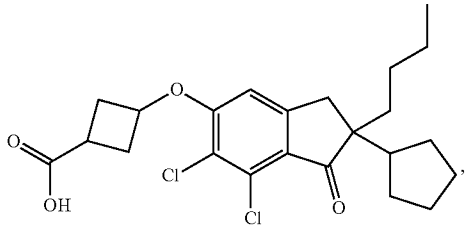
,
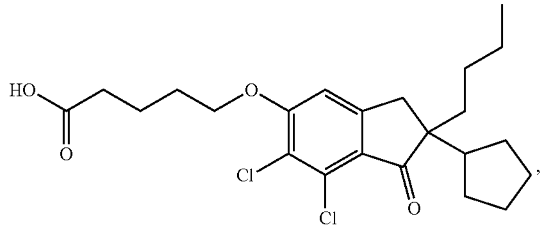
, and salts thereof.

In certain the embodiments described herein, the compound to be administered is selected from the group consisting of:

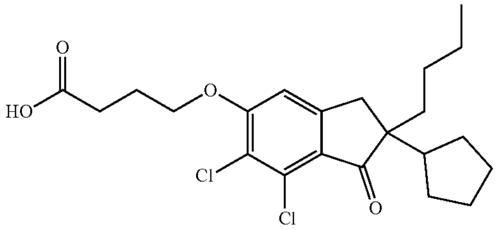
,
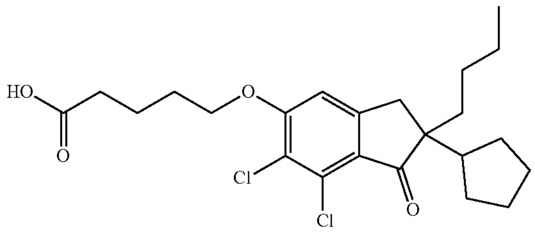
,

-continued

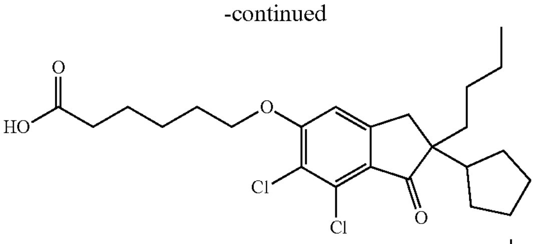

,

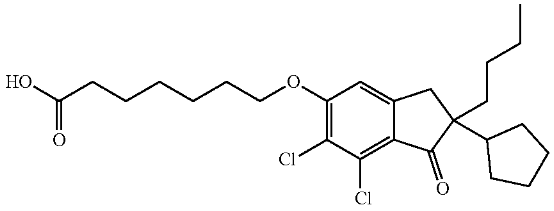

, and salts thereof.

In various embodiments, the methods of suppressing inflammasome activation include treating a disease or condition in which inflammation contributes to the disease or condition state (i.e., inflammatory diseases). Various inflammatory diseases that can be treated accordingly to the present methods include:

Rheumatologic and connective tissue diseases including rheumatic arthritis, systemic sclerosis, systemic lupus erythematosus, Sjogren syndrome, Reiter syndrome, systemic juvenile idiopathic arthritis, and spondyloarthropathies;

Systemic vasculitides including giant cell arteritis, polymyalgia rheumatics, Takayasu's arteritis, polyarteritis nodosa, Kawasaki disease, ANCA-associated vasculitis, immune complex-mediated vasculitis, Behcet syndrome, relapsing polychondritis, and sarcoidosis;

Dermatologic inflammatory diseases including psoriasis, psoriatic arthritis, eczema, chronic urticarial, neutrophilic dermatosis, and alopecia areata;

Sepsis/Systemic inflammatory response syndrome and acute respiratory distress syndrome;

Immunologic rejection of heart, lung, liver, kidney, pancreatic islet, and other solid organ transplants;

Immunologic rejection of bone marrow and other hematologic tissue transplants;

Inflammatory diseases of the heart including atherosclerosis, pericarditis, and myocarditis;

Inflammatory disease of the gastrointestinal system including inflammatory bowel disease including ulcerative colitis and Crohn's disease, nonalcoholic inflammatory bowel steatohepatitis and fibrosis, alcoholic hepatitis, and autoimmune hepatitis;

Glomerulonephritis, interstitial nephritis, anti-tubular basement membrane antibody-mediated tubulointerstitial nephritis, and IgG4-related disease;

Inflammatory disease of the lung including asthma, bronchitis, and pulmonary interstitial fibrosis, pneumonitis;

Auto-inflammatory diseases including familial Mediterranean fever, tumor necrosis factor receptor-associated periodic syndrome (TRAPS), familial cold auto-inflammatory syndrome, Muckle-Wells syndrome, and Schnitzler syndrome;

Inflammatory diseases of the central and peripheral nervous system including multiple sclerosis, chronic inflammatory demyelinating polyneuropathy, Guillain-Barre syndrome, multiple sclerosis, and idiopathic transverse myelitis;

Inflammatory myopathies including polymyositis, dermatomyositis, inclusion body myositis, immune-mediated necrotizing myopathy; and Thyroiditis.

In some embodiments, the method is for treating nonalcoholic steatosis, nonalcoholic fatty liver disease, obesity-induced insulin resistance, arthritis, inflammatory bowel disease, and/or coronary artery disease in a subject in need thereof.

Each of the states, diseases, disorders, and conditions, described herein, as well as others, can benefit from methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Methods of the present invention also relate to stabilizing SWELL1-LRRC8 hexamer assembly and trafficking to restore signaling. A pharmacological chaperone may assist in assembly and trafficking of SWELL1-LRRC8. The pharmacological chaperone can comprise a biologic or small molecule drug (e.g., compounds described herein).

The present invention further relates to a various small molecule or biologic pharmacological chaperone (e.g., compounds described herein). For example, the small molecule or biologic pharmacological chaperone can function as a molecular staple to bind together SWELL1-LRRC8 monomers. The small molecule or biologic pharmacological chaperone can function as a molecular glue to bind together SWELL1-LRRC8 monomers. The small molecule or biologic pharmacological chaperone can function to increase SWELL1-LRRC8 protein expression. The small molecule or biologic pharmacological chaperone can function to increase SWELL1-LRRC8 membrane translocation. Further, the small molecule or biologic pharmacological chaperone can function to increase SWELL1-LRRC8 signaling.

The small molecule or biologic pharmacological chaperone can also function to reduce SWELL1-LRRC8 degradation. The small molecule or biologic pharmacological can bind to the SWELL-LRRC8 complex at residue R103E in the pore and within a conserved hydrophobic pocket to bind the SWELL1-LRRC8 complex. The small molecule or biologic pharmacological chaperone can function to bind to multiple sites in the SWELL1-LRRC8 molecule to stabilize assembly and minimize degradation in the setting of metabolic syndrome. The small molecule or biologic can close or inhibit SWELL1-LRRC8 channel complexes. The small molecule or biologic can inhibit SWELL1-LRRC8 channel conductance.

In accordance with the various methods of the present invention, a pharmaceutical composition comprising a compound of Formula (I) is administered to the subject in need thereof. The pharmaceutical composition can be administered by a routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. In various embodiments, administration is selected from the group consisting of oral, intranasal, intraperitoneal, intravenous, intramuscular, rectal, and transdermal.

The determination of a therapeutically effective dose for any one or more of the compounds described herein is within the capability of those skilled in the art. A therapeutically effective dose refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease or condition state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Typically, the normal dosage amount of the compound can vary from about 0.05 to about 100 mg per kg body weight depending upon the route of administration. Guidance as to particular dosages and methods of delivery is provided in the literature and generally available to practitioners in the art. It will generally be administered so that a daily oral dose in the range, for example, from about 0.1 mg to about 75 mg, from about 0.5 mg to about 50 mg, or from about 1 mg to about 25 mg per kg body weight is given. The active ingredient can be administered in a single dose per day, or alternatively, in divided doses (e.g., twice per day, three time a day, four times a day, etc.). In general, lower doses can be administered when a parenteral route is employed. Thus, for example, for intravenous administration, a dose in the range, for example, from about 0.05 mg to about 30 mg, from about 0.1 mg to about 25 mg, or from about 0.1 mg to about 20 mg per kg body weight can be used.

A pharmaceutical composition for oral administration can be formulated using pharmaceutically acceptable carriers known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. In certain embodiments, the composition is formulated for parenteral administration. Further details on techniques for formulation and administration can be found in the latest edition of REMINGTON'S PHARMACEUTICAL SCIENCES (Mack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

In addition to the active ingredients (e.g., the compound of Formula (I)), the pharmaceutical composition can contain suitable pharmaceutically acceptable carriers comprising excipients and auxiliaries that facilitate processing of the active compounds into preparations which can be used pharmaceutically. As used herein, the term "pharmaceutically acceptable carrier" means a non-toxic, inert solid, semi-solid or liquid filler, diluent, encapsulating material, or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil; and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; artificial cerebral spinal fluid (CSF), and phosphate buffer solutions, as well as other non-toxic compatible lubricants such as sodium lauryl sulfate and magnesium stearate, as well as coloring agents, releasing agents, coating agents, sweetening, flavoring, and perfuming agents, preservatives and antioxidants can also be present in the composition, according to the judgment of the formulator based on the desired route of administration.

Figure 3:
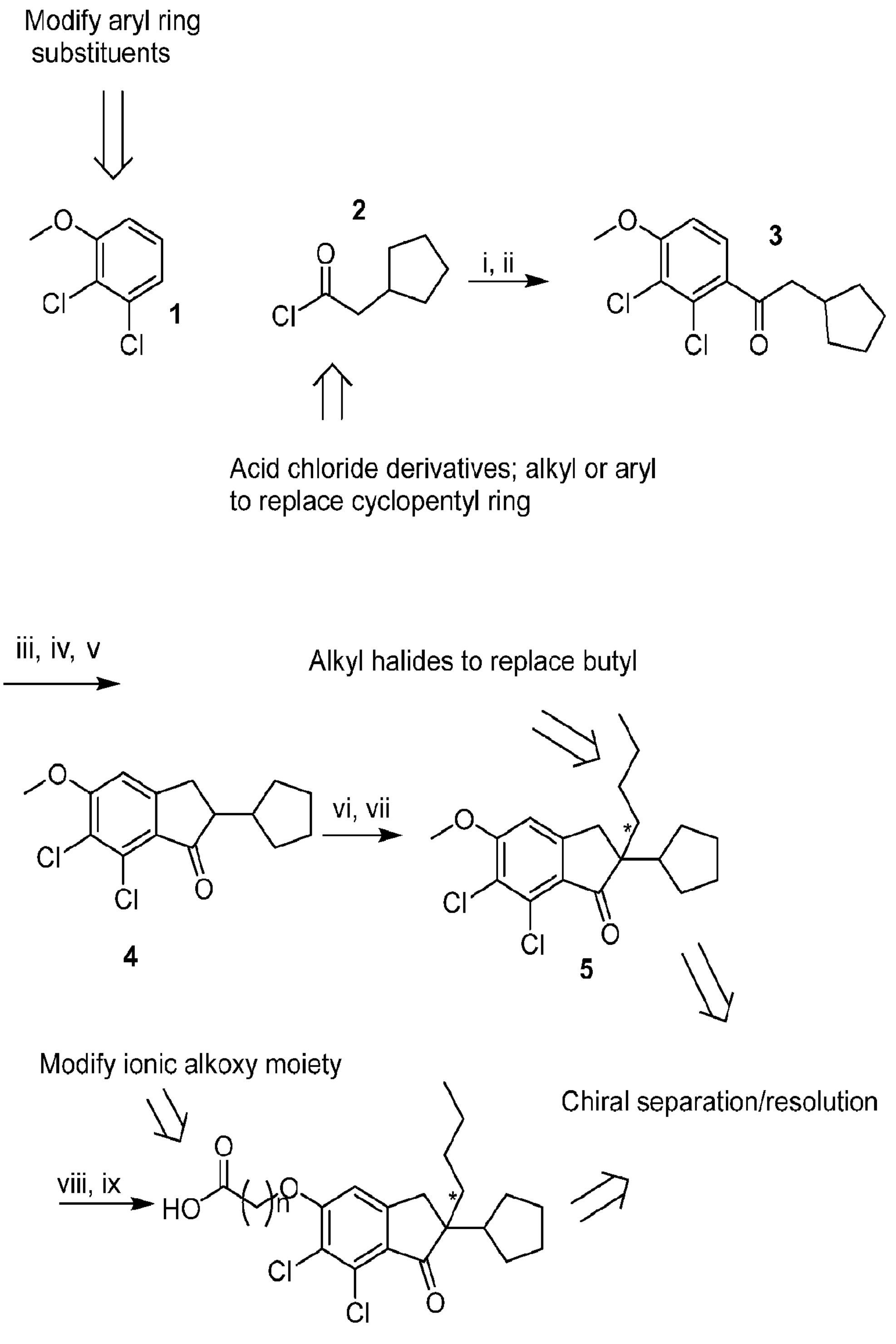
FIG. 3: Synthesis scheme for compounds described herein.

Synthesis of the compounds described herein is described in International Publication WO2020/252041 A1, which is hereby incorporated herein by reference for all relevant purposes. Further, various compounds described herein can be prepared according to the scheme shown in FIG. 3. Modifications to the synthetic scheme of FIG. 3 that can be made to synthesize a variety of compounds described herein are indicated by double arrows. Methods: i) $AlCl_3$, DCM, 5° C. to rt. ii) 12N HCl. iii) 1) Paraformaldehyde, dimethylamine, acetic acid, 85° C. iv) DMF, 85° C., v) $H_2SO_4$. vi) KOtBu, butyl iodide. vii) pyridine-HCl, 195° C. viii) $BrCH_2CO_2Et$, $K_2CO_3$, DMF, 60° C. ix) 10N NaOH.

Unless otherwise indicated, the alkyl, alkenyl, and alkynyl groups described herein preferably contains from 1 to 20 carbon atoms in the principal chain. They may be straight or branched chain or cyclic (e.g., cycloalkyls). Alkenyl groups can contain saturated or unsaturated carbon chains so long as at least one carbon-carbon double bond is present. Alkynyl groups can contain saturated or unsaturated carbon chains so long as at least one carbon-carbon triple bond is present. Unless otherwise indicated, the alkoxy groups described herein contain saturated or unsaturated, branched or unbranched carbon chains having from 1 to 20 carbon atoms in the principal chain.

Unless otherwise indicated herein, the term "aryl" refers to monocyclic, bicyclic or tricyclic aromatic groups containing from 6 to 14 ring carbon atoms and including, for example, phenyl. The term "heteroaryl" refers to monocyclic, bicyclic or tricyclic aromatic groups having 5 to 14 ring atoms and containing carbon atoms and at least 1, 2 or 3 oxygen, nitrogen or sulfur heteroatoms.

As referred to herein, the term "salts" includes various pharmaceutically acceptable salts thereof such as amine salts, lithium salts, sodium salts, potassium salts, and mixtures thereof.

EXAMPLES

The following non-limiting examples are provided to further illustrate the present invention.

Figure 4:
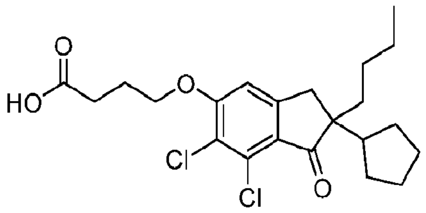
FIG. 4: Structures of compounds tested in Example 1.
Figure 4:
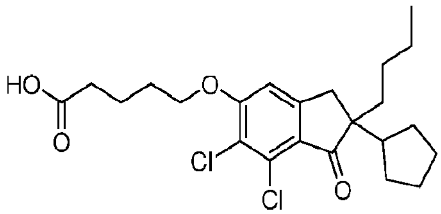
Figure 4:
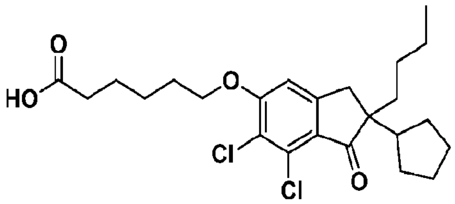
Figure 4:
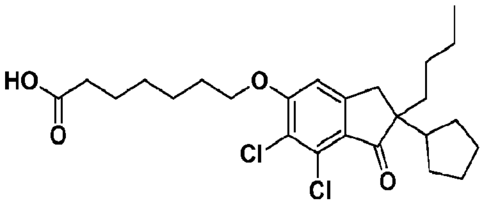
Figure 4:
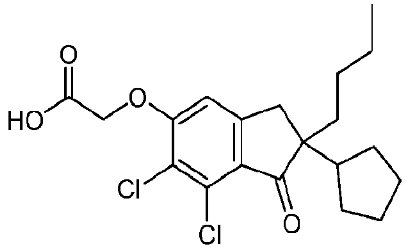
Figure 4:
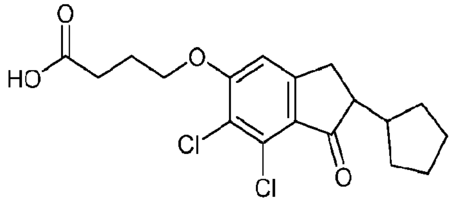
Figure 5:
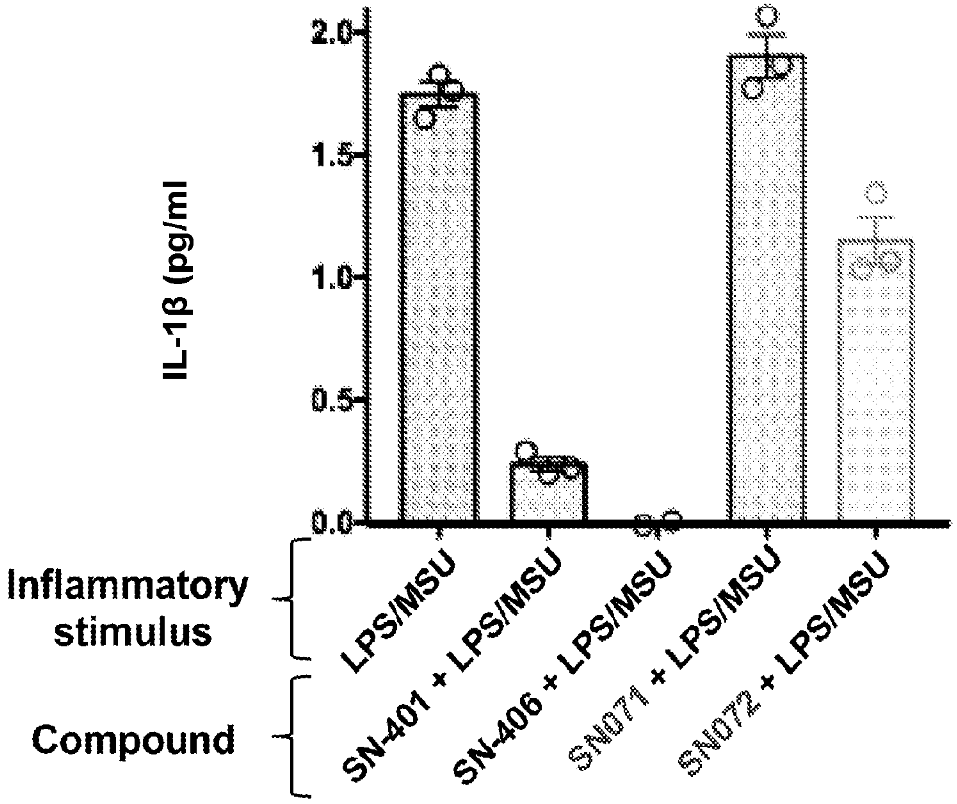
FIG. 5: SN-401 and SN-406 robustly inhibit macrophage inflammasome activation in response to LPS+MSU (mechanical stimulation).

Example 1: SN-401 and SN-406 Robustly Inhibit Macrophage Inflammasome Activation We directly tested macrophage inflammasome activation (IL-1β) in response to lipopolysaccharide (LPS) and LPS+ monosodium urate crystals (MSU, mechanical inflammatory stimulus) in the presence and absence of active SN-401, SN-406 and inactive SN071 and SN072 (negative controls). See FIG. 4 for the structures of the compounds. Mechanical stimulation by MSU crystals function as a physiological activation mechanism for the putatively mechanosensitive SWELL1-LRRC8 channel complex as macrophages engulf MSU and undergo large volume changes. This is analogous to cholesterol crystals that are thought to contribute to NASH by driving simple hepatic steatosis toward fibrotic steatosis. LPS priming followed by MSU robustly activates inflammasome mediated IL-1β secretion from primary macrophages, and this is fully suppressed by SWELL1-active SN-401 and SN-406, but not by inactive SN071/SN072 consistent with SWELL1 on-target mechanism of action (FIG. 5). These data indicate that SN-401 and active congeners possess anti-inflammatory activity. First-pass effect from oral delivery, combined with the fact that SN-40X are lipophilic carboxylic acids may conspire to increase hepatic drug concentrations sufficiently to exert anti-inflammatory activity on resident hepatic macrophages and Kupffer cells that contribute to steatohepatitis.

Figure 6:
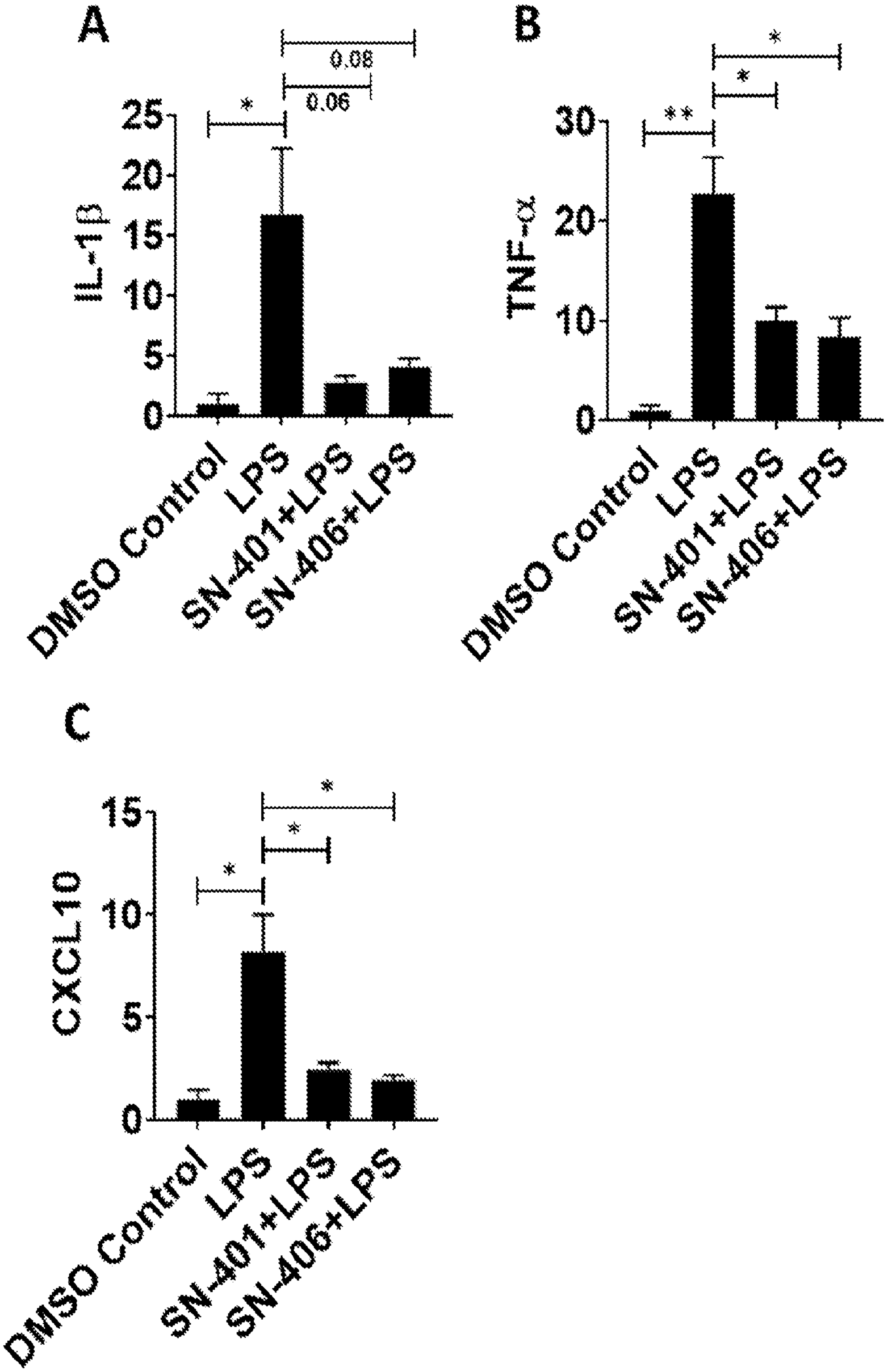
FIG. 6: Panels A-C show relative mRNA expression for selected inflammatory markers, IL1β, TNF-α and CXCL10 from 3 independent experiments.

Example 2: SWELL1-LRRC8 Modulators SN-401 and SN-406 Inhibit the Expression of LPS-Induced Inflammatory Cytokine Production RAW 264.7 cells were incubated with either vehicle (DMSO) or SN-401 (10 μM) and SN-406 (10 μM) for 2 hours and subsequently, cells were activated with either LPS (50 ng/ml) alone or along with SN-401 (10 μM) and SN-406 (10 μM) for 30 minutes. After the activation cells were harvested for qRT-PCR analysis (see FIG. 6, panels A-C). Relative mRNA expression for selected inflammatory markers, IL1β, TNF-α and CXCL10 from 3 independent experiments. Statistical significance between the indicated groups were calculated by using a two-tailed Student's t-test. Error bars represent mean ±s.e.m. *, $P<0.05$, , $P<0.01$, *, $P<0.001$, ****, $P<0.0001$.

Example 3: SWELL1 Currents in Primary Macrophages

Figure 7:
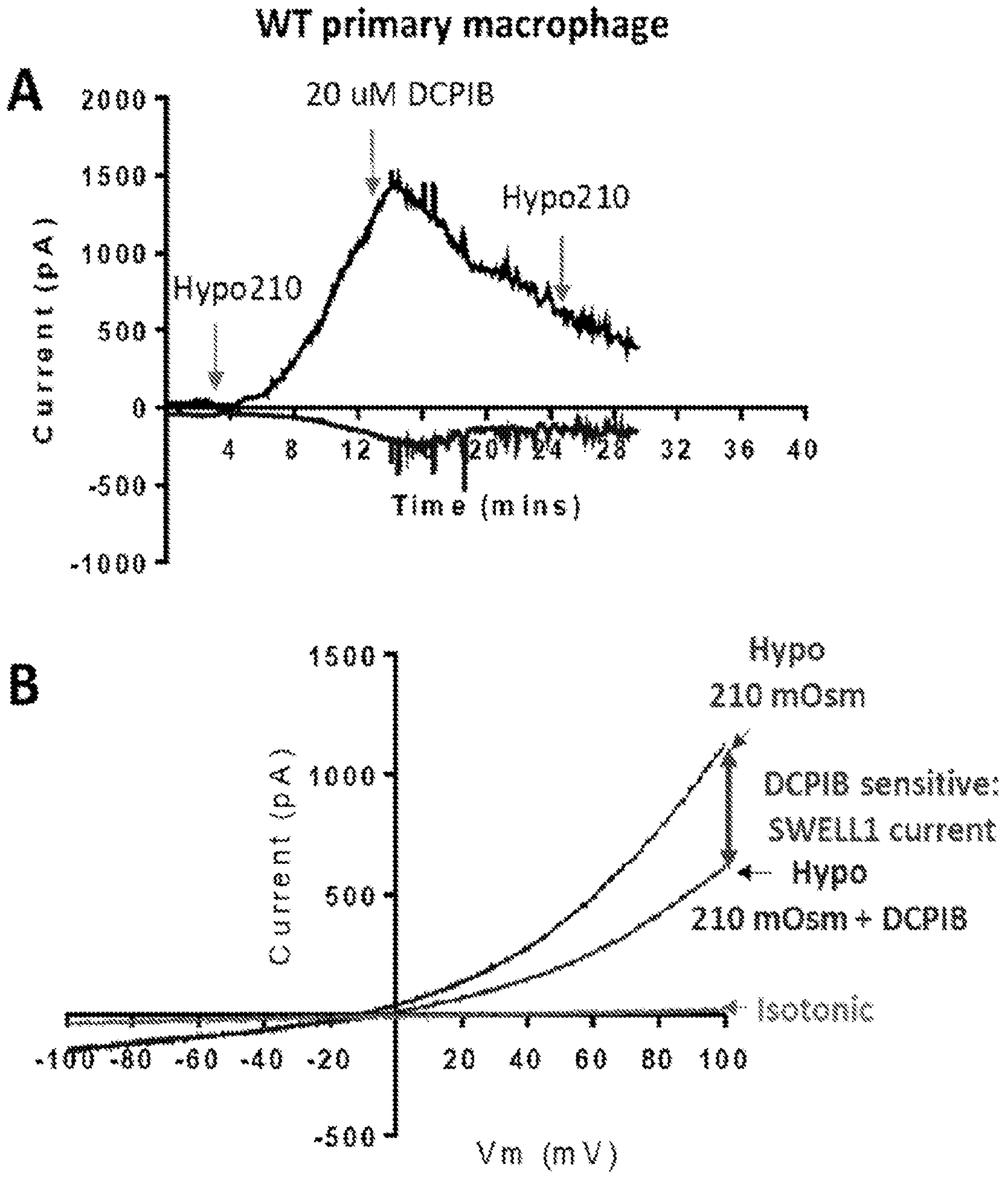
FIG. 7: Panel A, Current over time plots of hypotonically-induced currents in wild-type (WT) primary macrophages (210 mOsm) and inhibition by DCPIB revealing the DCPIB-sensitive SWELL1 current. Panel B, Current voltage plot from (A) above.
Figure 8:
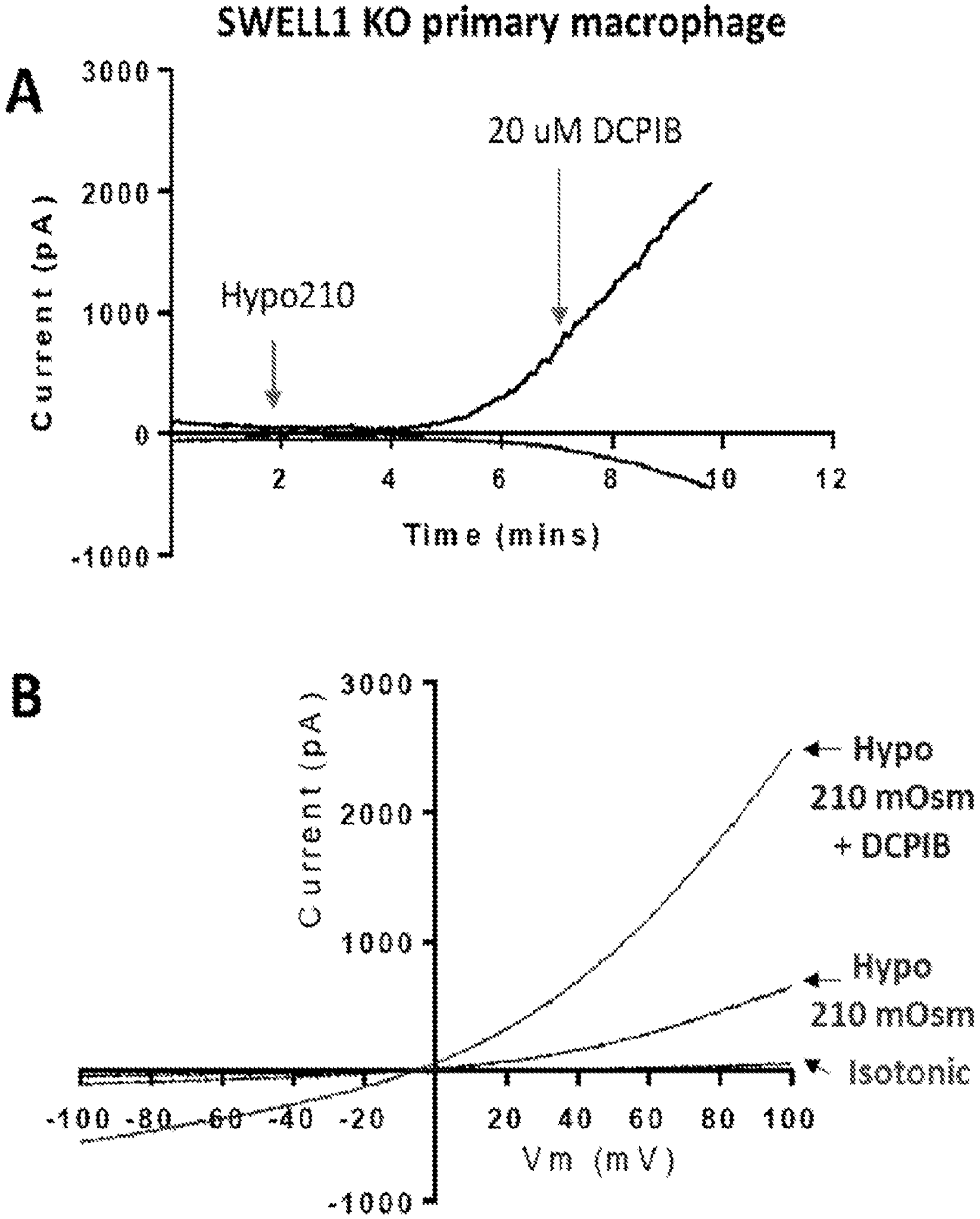
FIG. 8: Panel A, Current over time plots of hypotonically-induced currents in SWELL1 KO primary macrophages (210 mOsm) and no response with DCPIB, revealing no measurable DCPIB-sensitive, or SWELL1 currents. Panel B, Current voltage plot from (A) above.

Current over time of hypotonically-induced currents in wild-type (WT) primary macrophages (210 mOsm) was measured along with inhibition by DCPIB revealing the DCPIB-sensitive SWELL1 current. See FIG. 7 (Panel A, Current over time plot; Panel B, Current voltage plot from (A) above). Current over time of hypotonically-induced currents in SWELL1 KO primary macrophages (210 mOsm) was measured along with DCPIB response. No response with DCPIB was identified, revealing no measurable DCPIB-sensitive, or SWELL1 currents. See FIG. 8 (Panel A, Current over time plot; Panel B, Current voltage plot from (A) above).

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

Having described the invention in detail, it will be apparent that modifications and variations are possible without departing from the scope of the invention defined in the appended claims.

What is claimed is:

1. A method for suppressing inflammasome activation in a subject in need thereof, the method comprising administering to a subject a therapeutically effective amount of a compound of Formula (I), or a salt thereof:

(I)

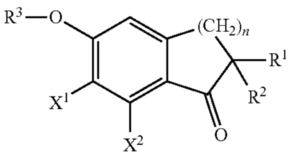

wherein $R^1$ is $C_1$-$C_6$ alkyl;

$R^2$ is cyclopentyl;

$R^3$ is -Y-C(O)$R^4$;

$R^4$ is —O$R^7$;

$X^1$ and $X^2$ are each independently alkyl or halo, is hydrogen or alkyl;

Y is

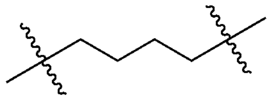
,
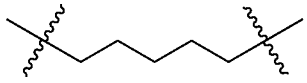
,
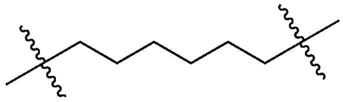
,
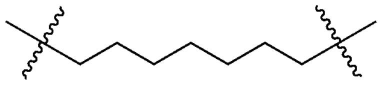
, or
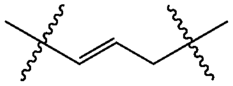
;

and n is 1 or 2.

2. The method of claim 1 wherein Y is selected from the group consisting of

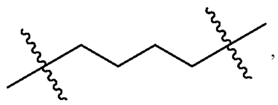
,
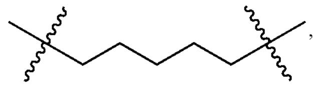
,
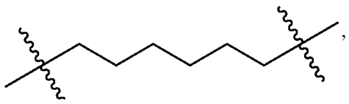
, and

-continued

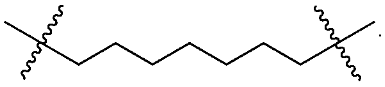

3. The method of claim 1 wherein $R^3$ is selected from the group consisting of:

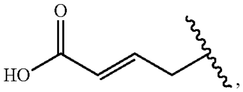,

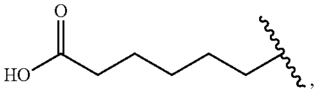,

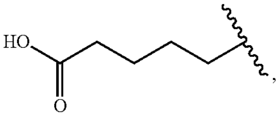, and

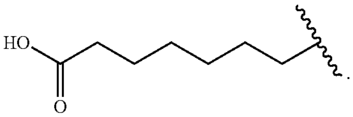.

4. The method of claim 1 wherein $X^1$ and $X^2$ are each independently selected from $C_1$ to $C_6$ alkyl, fluoro, chloro, bromo, or iodo.

5. A method for suppressing inflammasome activation in a subject in need thereof, the method comprising administering to a subject a therapeutically effective amount of a compound, or a salt thereof selected from the group consisting of:

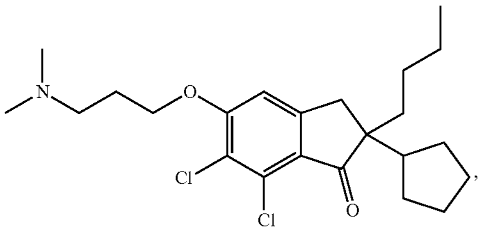,

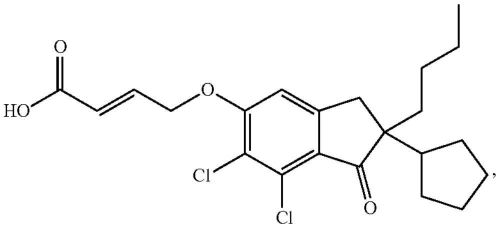,

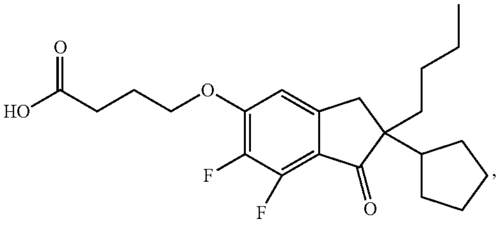,

-continued

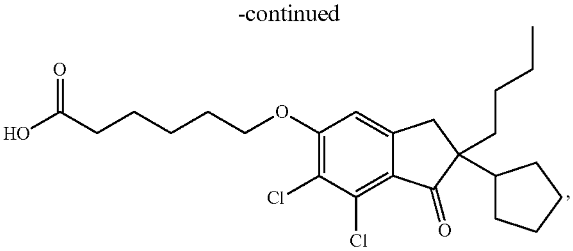,

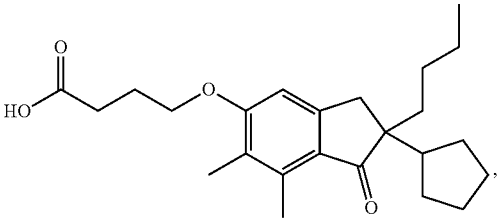,

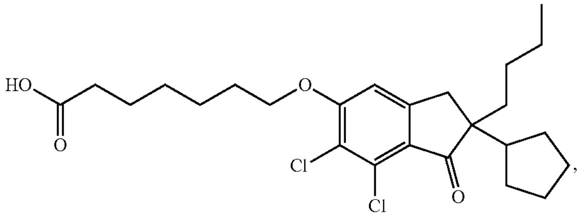,

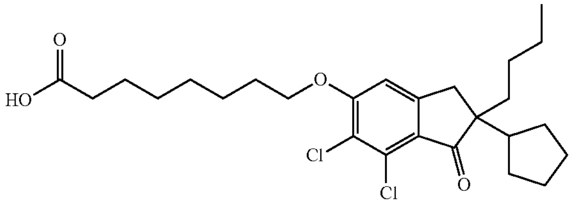,

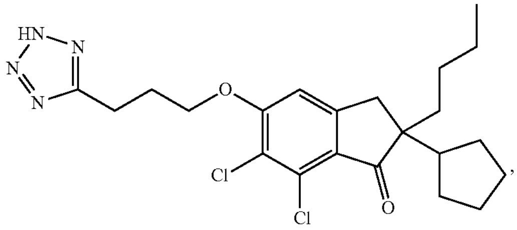,

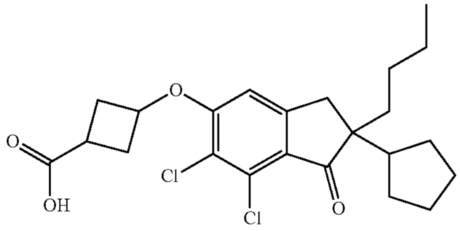 and

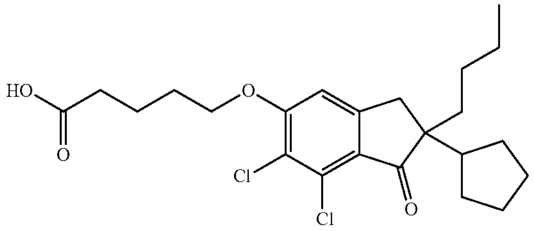.

6. The method of claim 1 wherein the subject has an inflammatory disease selected from the group consisting of a rheumatologic and connective tissue disease, a systemic vasculitide, sarcoidosis, a dermatologic inflammatory disease, sepsis/systemic inflammatory response syndrome, and acute respiratory distress syndrome.

7. The method of claim 1 wherein the subject has an inflammatory disease selected from atherosclerosis, pericarditis, and myocarditis.

8. The method of claim 1 wherein the subject has an inflammatory disease selected from ulcerative colitis, Crohn's disease, nonalcoholic inflammatory bowel steatohepatitis, fibrosis, alcoholic hepatitis, and autoimmune hepatitis.

9. The method of claim 1 wherein the subject has an inflammatory disease selected from glomerulonephritis, interstitial nephritis, anti-tubular basement membrane antibody-mediated tubulointerstitial nephritis, IgG4-related disease, asthma, bronchitis, and pulmonary interstitial fibrosis, pneumonitis, familial Mediterranean fever, tumor necrosis factor receptor-associated periodic syndrome (TRAPS), familial cold auto-inflammatory syndrome, Muckle-Wells syndrome, Schnitzler syndrome, multiple sclerosis, chronic inflammatory demyelinating polyneuropathy, Parkinson's disease, Guillain-Barre syndrome, multiple sclerosis, and idiopathic transverse myelitis.

10. The method of claim 1, wherein $R^1$ is butyl.

11. The method of claim 1, wherein $X^1$ and $X^2$ are each independently methyl, fluoro, or chloro.

* * * * *